US008609397B2

(12) United States Patent
Higashiyama

(10) Patent No.: US 8,609,397 B2
(45) Date of Patent: Dec. 17, 2013

(54) METHOD FOR PRESERVING A MICROORGANISM

(75) Inventor: Kenichi Higashiyama, Kobe (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 1373 days.

(21) Appl. No.: 11/631,872

(22) PCT Filed: Aug. 10, 2005

(86) PCT No.: PCT/JP2005/014960
§ 371 (c)(1),
(2), (4) Date: Jan. 8, 2007

(87) PCT Pub. No.: WO2006/016702
PCT Pub. Date: Feb. 16, 2006

(65) Prior Publication Data
US 2008/0038789 A1    Feb. 14, 2008

(30) Foreign Application Priority Data

Aug. 12, 2004  (JP) ................................ 2004-235551

(51) Int. Cl.
*C12N 1/04* (2006.01)
(52) U.S. Cl.
USPC ........ 435/260; 435/254.1; 435/171; 424/93.5
(58) Field of Classification Search
None
See application file for complete search history.

(56) References Cited

U.S. PATENT DOCUMENTS 6,337,411 B2    1/2002   Hopmann et al.

FOREIGN PATENT DOCUMENTS

| EP | 1 035 211 A1 | 9/2000 |
|---|---|---|
| JP | 63-012290 | 1/1988 |
| JP | 63-044891 | 2/1988 |
| JP | 05-009188 | 1/1993 |
| JP | 05-091886 | 4/1993 |
| JP | 05-091887 | 4/1993 |
| JP | 05-091888 | 4/1993 |
| JP | 06-153970 | 6/1994 |
| JP | 10-057085 | 3/1998 |
| JP | 11-243981 | 9/1999 |
| JP | 2003-048831 | 2/2003 |
| WO | WO 91/07498 | 5/1991 |
| WO | 98/29558 | 7/1998 |
| WO | WO 02/46386 A2 | 6/2002 |

OTHER PUBLICATIONS

Higashiyama K et al: "Enhancement of arachidonic acid production by *Mortierella alpine* IS-4" Journal of the American Oil Chemists' Society, vol. 75, No. 11, Nov. 1998, pp. 1501-1505.*
Hoffmann et al., Technical Information Sheet No. 5, 1991, pp. 92-94.*

European Search Report issued Dec. 19, 2007, in European Application No. 05 772 543.4.
Phillips, "A discussion of lesser-known and complex laboratory techniques for the efficient revival, propagation and preservation of fungal cultures," Phytopathology, vol. 91, No. 6, Jun. 2001, p. S120.
Stanbury et al., "Principles of Fermentation Technology," Pergamon Preses, 1984, pp. 31-33, A. Wheaton & Co., Ltd., Exeter, Great Britain which was translated into Japanese by F. Ishizaki, Center for Academic Publications, Japan, Hakko Kogaku no Kiso [Fundamentals of Fermentation Engeineering] (1988).
Third Party Observations in related Japanese Application No. 2007-525500 in Japanese.
Uemura et al., "Fermentation and Microorganism II" (Sadajiro Uemura and Hiroshi Souda, editors, Asakura Publishing Col., Ltd.) Oct. 10, 1970 (with partial English-language translation).
Chapter 2, "Method of Strain Preservation" In Fermentation Engineering, Progress in the $20^{th}$ Century—Exploration of Origin of Biotechnology, Dec. 25, 2000, The Society for Biotechnology, Japan, (with partial English-language translation).
Suzuki et al., "Methods for classification and identification of microorganisms—general approaches to molecular genetic and molecular biological technique," Sep. 16, 2001,(Kenichiro Suzuki, Akira Hiraishi, and Akira Yokota editors, Springer Verlag Tokyo) (with partial English-language translation).
Higashiyama et al., Image Analysis of Morphological Change during Arachidonic Acid Production by *Mortierella alpina* 1S-4, Journal of Bioscience and Bioengineering, vol. 87, No. 4, 1999, pp. 489-494.
Hasegawa et al., "History and Evolution of Culture Maintenance and Preservation Techniques", in Maintaining Cultures for Biotechnology and Industry, 1996, Academic Press, Chapter 2, pp. 15-27.
Smith et al., "Fungi", in Maintaining Cultures for Biotechnology and Industry, 1996, Academic Press, Chapter 6, pp. 101-132.
International Search Report mailed Nov. 17, 2005 in International PCT Application No. PCT/J02005/014960.
Higashiyama et al., "Enhancement of Arachidonic Acid Production by *Mortierella alpina* 1S-4," Journal of the American Oil Chemists' Society, vol. 75, No. 11, Nov. 1998, pp. 1501-1505.
Higashiyama et al., "Effects of Mineral Addition on the Growth Morphology of and Arachidonic Acid Production by *Mortierella alpina* 1S-4," Journal of the American Oil Chemists' Society, vol. 75, No. 12, Dec. 1998, pp. 1815-1819.
Park et al., "Morphological Diversity of *Mortierella alpina*: Effect of Consumed Carbon to Nitrogen Ratio in Flask Culture," Biotechnology and Bioprocess Engineering, vol. 6, No. 3, 2001, pp. 161-166.
Monaghan et al., "Culture Preservation and Inoculum Development," Manual of industrial microbiology and biotechnology—$2^{nd}$ edition, 1999, ASM Press, pp. 29-48.
Higashiyama et al., "Production of Arachidonic Acid by *Mortierella* Fungi," Biotechnology and Bioprocess Engineering, vol. 7, No. 5, Sep. 2002, pp. 252-262.

* cited by examiner

*Primary Examiner* — Irene Marx
(74) *Attorney, Agent, or Firm* — Drinker Biddle & Reath LLP

(57) ABSTRACT

A method for preservation of a microorganism capable of microbial production of a polyunsaturated fatty acid or a compound comprising a polyunsaturated fatty acid as a constituent fatty acid, which method comprises: (a) forming spores in a spore-forming medium at pH 4-7 containing a nutrient source comprising an inorganic salt and a saccharide; (b) suspending the spores obtained in (a) in sterilized water, or sterilized water containing a surfactant and/or an inorganic salt to prepare a spore suspension, and adding a cryoprotectant at 5-15% to prepare a cryopreserving spore suspension; and (c) preserving the cryopreserving spore suspension obtained in (b) at between −100° C. and −20° C.

9 Claims, No Drawings

METHOD FOR PRESERVING A MICROORGANISM

CROSS REFERENCE TO RELATED APPLICATIONS

This application is a National Stage of International Application No. PCT/JP2005/014960 filed Aug. 10, 2005, and which claims benefit of Japanese Patent Application No. 2004-235551 filed Aug. 12, 2004, and are incorporated by reference herein in their entirety.

TECHNICAL FIELD

The present invention relates to a method for production of a microbial biomass which includes microorganisms that produce compounds comprising polyunsaturated fatty acids as constituent fatty acids, crude oils and/or crude phospholipids obtained by extraction from the biomass, and refined fats and oils and/or refined phospholipids obtained by refining of the crude oils and/or crude phospholipids, as well as to foods and beverages, therapeutic nutritional supplements, animal feeds and pharmaceuticals which incorporate the biomass and fats or oils (crude oils and/or refined oils) and/or phospholipids (crude phospholipids and/or refined phospholipids).

BACKGROUND ART

Biosynthesis of polyunsaturated fatty acids (hereinafter abbreviated as "PUFA") in humans occurs for two representative series, the $\omega 3$ and $\omega 6$ series (where $\omega$ represents the number of the carbon atom having the first double bond, counting from the methyl group end of the fatty acid), and in the case of $\omega 6$ fatty acids, for example, linoleic acid (18:2 $\omega 6$) is converted to $\gamma$-linolenic acid (18:3 $\omega 6$), dihomo-$\gamma$-linolenic acid (20:3 $\omega 6$), arachidonic acid (20:4 $\omega 6$) and 4,7,10,13,16-docosapentaenoic acid (22:5 $\omega 6$), by repeated desaturation and carbon chain elongation.

Similarly, in the case of $\omega 3$ fatty acids, $\alpha$-linolenic acid (18:3 $\omega 3$) is converted to eicosapentaenoic acid (20:5 $\omega 3$), 7,10,13,16,19-docosapentaenoic acid (22:5 $\omega 3$) and 4,7,10,13,16,19-docosapentaenoic acid (22:6 $\omega 3$), by repeated desaturation and carbon chain lengthening. The $\omega 3$ PUFAs eicosapentaenoic acid (hereinafter, "EPA") and docosapentaenoic acid (hereinafter, "DHA") in particular are known to have numerous physiological functions including prophylactic effects against adult diseases such as atherosclerosis and thrombosis or anticancer effects, as well as learning reinforcement effects, and various attempts have been made to utilize them in pharmaceuticals and specific health foods. However, the physiological functions of PUFAs other than $\omega 3$ types (such as $\omega 6$ and $\omega 9$) have recently also been the subject of attention.

Arachidonic acid constitutes approximately 10% of the fatty acid components of vital organs such as the blood and liver (for example, the fatty acid compositional ratio of the phospholipids in human blood is 11% arachidonic acid, 1% eicosapentaenoic acid, 3% docosapentaenoic acid), and as a major structural component of cell membranes, it contributes to modulating membrane fluidity and performs various metabolic functions in the body, while also playing an important role as a direct precursor of prostaglandins. Recently the roles of arachidonic acid as a nursing infant nutrient and as a constituent fatty acid of endogenous cannabinoids which exhibit neurergic effects (2-arachidonoyl monoglycerol and anandamide) have been noted. Normally, ingestion of linoleic acid-rich foods leads to their conversion to arachidonic acid, but since the functions of the enzymes involved in its biosynthesis are reduced in patients with adult diseases or preliminary conditions as well as in infants and the elderly, such individuals tend to be deficient in arachidonic acid; it has therefore been desirable to provide means for its direct ingestion in the form of a constituent fatty acid of fats or oils (triglycerides).

Although fish oils are abundant sources of $\omega 3$ PUFAs such as EPA and DHA, $\omega 6$ PUFAs such as $\gamma$-linolenic acid, dihomo-$\gamma$-linolenic acid, arachidonic acid and 4,7,10,13,16-docosapentaenoic acid (22:5 $\omega 6$) are virtually unobtainable from traditional fat or oil sources, and therefore fats and oils comprising PUFAs as constituent fatty acids (hereinafter referred to as "PUFA-containing fats and oils") obtained by fermentation of microorganisms are most commonly used at the current time. For example, methods have been proposed for obtaining fats and oils comprising arachidonic acid as a constituent fatty acid (hereinafter referred to as "arachidonic acid-containing fats and oils") by culturing of various microorganisms capable of producing arachidonic acid-containing fats and oils.

It is known that fats and oils having a high proportion of arachidonic acid constituting the fatty acid portion (hereinafter referred to as "arachidonic acid-rich fats and oils") can be obtained by using microorganisms belonging to the genus *Mortierella*

(Japanese Unexamined Patent Publication SHO No. 63-44891, Japanese Unexamined Patent Publication SHO No. 63-12290). In recent years, one of the essential uses of arachidonic acid is in the field of nursing infant nutrition, for example, and specifically the use of arachidonic acid-containing fats and oils obtained by fermentation in modified milk has been introduced. New effects of arachidonic acid-containing fats and oils have also been demonstrated (Japanese Unexamined Patent Publication No. 2003-48831: Composition with prophylactic or ameliorative effect on symptoms and conditions associated with brain function impairment), and these are expected to be in high demand in the future.

Fats and oils obtained by culturing of *Mortierella* microorganisms largely consist of triglycerides (approximately 70% or greater) and phospholipids. The edible fats and oils are in the form of triglycerides, and for the purpose of the use described above, the original fats and oils produced by the cells (fats and oils obtained by extraction from cells, known as "crude oils") are extracted from the cell biomass produced by culturing of the microorganisms, and then the crude oils are subjected to edible fat/oil refining steps (degumming, deoxidation, deodorization, decolorizing) to obtain refined fats and oils minus the phospholipids.

Since PUFA-containing fats and oils obtained by culturing of *Mortierella* microorganisms accumulate in hyphae, culturing must be carried out to a higher concentration to increase the yield of the PUFA-containing fats and oils per culture, for increased economy of the fat/oil production. The PUFA-containing fat and oil yield per culture is the product of the cell concentration and the PUFA-containing fat/oil content per cell, and it is therefore necessary to increase both the cell concentration and the PUFA-containing fat/oil content per cell. The cell concentration can be increased by raising the concentration of the medium nitrogen source, which is normally converted to cell components.

The PUFA-containing fat/oil content per cell can only be increased by satisfactorily controlling the cell morphology and by carrying out the culturing with an adequate oxygen supply. Methods reported for controlling the cell morphology include optimization of the medium salt composition (Japanese Domestic Re-publication No. 98/029558), while methods of supplying oxygen include pressurized culturing methods and oxygen enriched aerobic culturing methods (Japanese Unexamined Patent Publication HEI No. 06-153970). However, since these methods are affected by slight differences in the culturing conditions, it is not easy to ensure reproducibility of culturing and as a result, stable production output has not been possible to achieve.

Patent document 1: Japanese Unexamined Patent Publication SHO No. 63-44891
Patent document 2: Japanese Unexamined Patent Publication SHO No. 63-12290
Patent document 3: Japanese Unexamined Patent Publication No. 2003-48831
Patent document 4: Japanese Domestic Re-publication No. 98/029558
Patent document 5: Japanese Unexamined Patent Publication HEI No. 06-153970

DISCLOSURE OF THE INVENTION

Thus, in order to ensure stable production of PUFA-containing fats and oils by microorganisms, it is highly desirable to develop a method for ensuring reproducibility of culturing.

The present inventors conducted diligent research on the initial culturing stage conditions affecting the cultured cell growth phase during production of PUFA-containing fats and oils (triglycerides) and/or PUFA-containing phospholipids by culturing of microorganisms, and as a result discovered that by improving the transplanting conditions for hyphae or spores from previous steps, it is possible to increase the reproducibility of culturing and to achieve stable production of PUFA-containing fats and oils (triglycerides) and/or PUFA-containing phospholipids.

According to the invention, therefore, there is provided a method for production of PUFA-containing fats and oils (triglycerides) and/or PUFA-containing phospholipids and/or PUFA-containing cells is based on improved reproducibility of culturing and stable production of PUFA-containing fats and oils (triglycerides) and/or PUFA-containing phospholipids, the method being characterized by improving the transplanting conditions for hyphae or spores from previous steps.

Specifically, the present invention provides a method for preservation of microorganisms capable of microbial production of polyunsaturated fatty acids or compounds comprising polyunsaturated fatty acids as constituent fatty acids, which method comprises:

(a) forming spores in a spore-forming medium at pH 4-7 containing a nutrient source comprising inorganic salts and saccharides;

(b) suspending the spores obtained in (a) above in sterilized water, or sterilized water containing a surfactant and/or inorganic salts to prepare a spore suspension, and adding a cryoprotectant at 5-15% to prepare a cryopreserving spore suspension; and (c) preserving the cryopreserving spore suspension obtained in (b) above at between −100° C. and -20° C.

In this method, the inorganic salts are preferably one or more inorganic salts selected from the group consisting of sodium nitrate, dipotassium hydrogen phosphate, magnesium sulfate, potassium chloride and iron (II) sulfate, and the spore-forming medium is preferably a Czapek agar medium or Czapek-Dox agar medium adjusted to a pH of 4-7.

The cryoprotectant used for this method is preferably glycerin.

Examples of polyunsaturated fatty acids or compounds comprising polyunsaturated fatty acids as constituent fatty acids include triglycerides comprising polyunsaturated fatty acids as constituent fatty acids and phospholipids comprising polyunsaturated fatty acids as constituent fatty acids, where the polyunsaturated fatty acids are preferably ω6 unsaturated fatty acids, ω3 polyunsaturated fatty acids or ω9 polyunsaturated fatty acids, or combinations thereof.

The aforementioned ω6 unsaturated fatty acids are preferably 9,12-octadecadienoic acid (linoleic acid) 18:2ω6, 6,9,12-octadecatrienoic acid (γ-linolenic acid) 18:3ω6, 8,11,14-eicosatrienoic acid (dihomo-γ-linolenic acid) 20:3ω6, 5,8,11,14-eicosatetraenoic acid (arachidonic acid) 20:4ω6, 7,10,13,16-docosatetraenoic acid 22:4ω6 or 4,7,10,13,16-docosapentaenoic acid 22:5ω6.

The aforementioned ω3 unsaturated fatty acids are preferably 9,12,15-octadecatrienoic acid (α-linolenic acid) 18:3ω3, 6,9,12,15-octadecatetraenoic acid (stearidonic acid) 18:4ω3, 11,14,17-eicosatrienoic acid (dihomo-α-linolenic acid) 20:3ω3, 8,11,14,17-eicosatetraenoic acid 20:4ω3, 5,8,11,14,17-eicosapentaenoic acid 20:5ω3, 7,10,13,16,19-docosapentaenoic acid 22:5ω3 or 4,7,10,13,16,19-docosahexaenoic acid 22:6ω3.

The aforementioned ω9 unsaturated fatty acids are preferably 6,9-octadecadienoic acid 18:2ω9, 8,11-eicosadienoic acid 20:2ω9 or 5,8,11-eicosatrienoic acid (Mead acid) 20:3ω9.

The microorganism used for the method described above is preferably one belonging to the genus *Mortierella*, such as *Mortierella alpina*.

The present invention relates to a method for production of polyunsaturated fatty acids or compounds comprising polyunsaturated fatty acids as constituent fatty acids, characterized by using microorganisms preserved by the method described above.

BEST MODE FOR CARRYING OUT THE INVENTION

More specifically, one of the features of time-dependent change of *Mortierella* filamentous fungi in liquid culture is increase in cellular mass by cell proliferation (cell growth stage). Intracellular accumulation of PUFA-containing fats and oils increases after the increase in cellular mass has essentially ceased (fat/oil accumulation stage), eventually resulting in abundant intracellular accumulation of PUFA-containing fats and oils. The present inventors have already reported culturing with a cell growth phase of approximately two days followed by six days of the fat/oil accumulation stage (J. Biosci. Bioeng., 87:489-494 (1999)).

It was also reported that the cell morphology is essentially determined during the cell growth phase, suggesting the extreme importance of setting and managing the initial culturing conditions. However, even though it appears to be important to set and manage the initial culturing conditions, no published reports can be found with regard to setting of the initial culturing conditions, and particularly the transplanting conditions for hyphae or spores. Focusing on this aspect, the present inventors conducted diligent research which led to the discovery that the transplanting method has a major effect on the results of culturing and that improving the transplanting method contributes significantly to improving the productivity of PUFA-containing fats and oils.

In order to obtain compounds comprising polyunsaturated fatty acids as constituent fatty acids (PUFA-containing fats and oils and/or PUFA-containing phospholipids) by liquid culturing of microorganisms, a small amount of cells of the preserved strain are first seeded in the culture solution and allowed to proliferate (first seed culturing stage). Next, scaling-up is accomplished by successive transfer to large-volume media, and the main culturing is the final step of culturing in which the microbial mass is recovered to obtain the PUFA-containing fats and oils. The seed culturing is the culturing at each stage during scaling-up by successive sub-culturing.

Known methods of preserving cells include methods wherein cells cultured on agar slant medium are preserved in a 5° C. refrigerator or a −20° C. freezer, methods wherein a filamentous fungal spore suspension is preserved in a 5° C. refrigerator, methods wherein a cryoprotectant is added and the cells are preserved in a liquid nitrogen freezer or at an ultra low temperature of between −150° C. and −196° C. created with liquid nitrogen, methods wherein cells are soil cultured and dried, and methods wherein cells are freeze-dried and refrigerated ("Hakko Kogaku no Kiso [Fundamentals of Fermentation Engineering]" (1988), translated by Ishizaki, F., Center for Academic Publications, Japan).

Also, "Maintaining cultures for Biotechnology and Industry (1996)", edited by J.C. Hunter-Cevera & A. Belt, Academic Press, compares −20° C. preservation at a slant, liquid nitrogen preservation and freeze-dried preservation and summarizes the effects on survival rates and productivity maintenance. According to this report, methods of slant preservation at −20° C. provide the most satisfactory survival rates and productivity maintenance (p. 25).

For filamentous fungi, the report teaches that it is difficult to stably maintain the cells in a live, pure state, and that although no method' exists which can be broadly applied to all filamentous fungi, preservation in liquid nitrogen may be considered ideal (ibid, p. 105). A list of examples of using various cryoprotectants is also given, and all of the prior art techniques are combinations of liquid nitrogen preservation or freeze-drying (ibid, p. 118, Table 4). Since the boiling point of liquid nitrogen at 1 atmospheric pressure is −195.8° C., the temperature in the liquid nitrogen storage tube is kept at about −196° C.

For filamentous fungi of the genus *Mortierella*, the preservation method and method of transfer to seed culture used is slant refrigerating preservation on Czapek agar medium, in an article by the present inventors (J. Am. Oil Chem. Soc., 75:1501-1505 (1998)). In an article by Park et al. (Biotechnol. Bioprocess Eng., 6:161-166 (2001)), the method employed involves preparation of a spore suspension at $10^3$ spores/mL by agar medium slant and transfer thereof to medium.

In light of the major importance of setting and managing the conditions for the initial culturing, the present inventors also focused on and diligently researched the importance of cell preservation which likely affects the initial culturing. As a result, it was discovered that a method of adding a cryoprotectant and preserving the mixture at between −100° C. and −20° C. is effective as a new method distinct from slant preservation, liquid nitrogen preservation or freeze-drying which have been reported in prior literature, while a method for preparing excellent spore suspensions was also discovered.

It is an object of the present invention to provide a method for production of PUFA-containing fats and oils (triglycerides) and/or PUFA-containing phospholipids and/or PUFA-containing cells, whereby PUFA-containing fats and oils (triglycerides) and/or PUFA-containing phospholipids are produced in a stable manner with improved reproducibility of culturing, the method being characterized by transferring and culturing cells preserved by a novel preserved cell preparation method and preservation method.

The present invention relates to production of compounds comprising polyunsaturated fatty acids as constituent fatty acids (fats and oils (triglycerides) and/or phospholipids) and to a method for production of microbial cells which produce the compounds (fats and oils (triglycerides) and/or phospholipids), by transfer and culturing of cells preserved by a novel preserved cell preparation method and preservation method.

Thus, culturing of a microorganism capable of producing compounds comprising polyunsaturated fatty acids as constituent fatty acids (fats/oils (triglycerides) and/or phospholipids) is essential. The microorganism referred to here is preferably a microorganism which produces at least one type of polyunsaturated fatty acid from among ω6 polyunsaturated fatty acids having 18 or greater number of carbon and three or more double bonds, ω9 polyunsaturated fatty acids having 18 or greater number of carbon and two or more double bonds and ω3 polyunsaturated fatty acids having 18 or greater number of carbon and three or more double bonds, as the major constituent fatty acid of the triglycerides and/or phospholipids.

As ω6 polyunsaturated fatty acids having 18 or greater number of carbon and three or more double bonds there may be mentioned γ-linolenic acid (6,9,12-octadecatrienoic acid), dihomo-γ-linolenic acid (8,11,14-eicosatrienoic acid), arachidonic acid (5,8,11,14-eicosatetraenoic acid), 7,10,13,16-docosatetraenoic acid (22:4 ω6) and DPAω6 (4,7,10,13,16-docosapentaenoic acid), as ω9 polyunsaturated fatty acids having 18 or greater number of carbon and two or more double bonds there may be mentioned 6,9-octadecadienoic acid, 8,11-eicosadienoic acid and Mead acid (5,8,11-eicosatrienoic acid), and as ω3 polyunsaturated fatty acids having 18 or greater number of carbon and three or more double bonds there may be mentioned α-linolenic acid (9,12,15-octadecatrienoic acid), 6,9,12,15-octadecatetraenoic acid (18:4ω3), 8,11,14,17-eicosatetraenoic acid (20:4ω3), EPA (5,8,11,14,17-eicosapentaenoic acid), DPAω3 (7,10,13,16,19-docosapentaenoic acid) and DHA (4,7,10,13,16,19-docosahexaenoic acid).

According to the invention, therefore, any microorganism may be used which can produce a compound comprising a polyunsaturated fatty acid as a constituent fatty acid (fat/oil (triglyceride) and/or phospholipid). As examples of microorganisms capable of producing oils and fats (triglycerides) containing arachidonic acid as a constituent fatty acid there may be mentioned fungi belonging to the genera *Mortierella, Conidiobolus, Pythium, Phytophthora, Penicillium, Cladosporium, Mucor, Fusarium, Aspergillus, Rhodotorula, Entomophthora, Echinosporangium* and *Saprolegnia*.

As examples of fungi belonging to the genus *Mortierella*, subgenus *Mortierella*, there may be mentioned *Mortierella elongata, Mortierella exigua, Mortierella hygrophila* and *Mortierella alpina*. More specifically, there may be mentioned the strains *Mortierella elongata* IFO8570, *Mortierella exigua* IFO8571, *Mortierella hygrophila* IFO5941, and *Mortierella alpina* IFO8568, ATCC16266, ATCC32221, ATCC42430, CBS219.35, CBS224.37, CBS250.53, CBS343.66, CBS527.72, CBS529.72, CBS608.70, CBS754.68, etc.

As examples of microorganisms capable of producing DHA there may be mentioned microorganisms belonging to the genera *Crypthecodenium, Thrautochytrium, Schizochytrium, Ulkenia, Japonochytrium* and *Haliphthoros*.

All of these strains may be acquired without any special restrictions from the Institute for Fermentation, Osaka (IFO), American Type Culture Collection (ATCC) or Centralbureau voor Schimmelcultures (CBS). There may also be used the strains *Mortierella alpina* 1S-4 and *Mortierella elongata* SAM0219 (FERM-P 8703) (FERM-BP 1239), isolated from soil by the research group for the present invention.

For culturing of a strain to be used for the invention, it is necessary to first prepare preserved cells of the obtained strain. The method of preparing the preserved cells involves first preparing a spore-forming medium. The spore-forming medium is produced by preparing a medium comprising some or all of the following components: sodium nitrate, dipotassium hydrogen phosphate, magnesium sulfate, potassium chloride and iron (II) sulfate, with saccharides, and adjusting the pH to the range of 4-7, and preferably 5-6.5. After adding agar to the prepared medium and conducting heat sterilization, the cooled solid is used as the spore-forming medium. The spore-forming medium is not particularly restricted so long as it allows hyphal growth and spore formation, but it is generally characterized by having a pH range of 4-7 which is suitable for spore formation.

As a specific example, there may be mentioned a medium obtained by adding hydrochloric acid or sulfuric acid to Czapek agar medium (2 g/L sodium nitrate, 1 g/L dipotassium hydrogen phosphate, 0.5 g/L magnesium sulfate heptahydrate, 0.5 g/L potassium chloride, 0.01 g/L iron (II) sulfate heptahydrate, 30 g/L saccharose, 13 g/L agar), to adjust the pH to 6.0. As another example there may be mentioned a medium obtained by adding hydrochloric acid or sulfuric acid to Czapek-Dox agar medium (2 g/L sodium nitrate, 1 g/L dipotassium hydrogen phosphate, 0.5 g/L magnesium sulfate heptahydrate, 0.5 g/L potassium chloride, 0.01 g/L iron (III) sulfate heptahydrate, 30 g/L glucose, 13 g/L agar), to adjust the pH to 6.0.

This method is used to prepare a slant medium or a plate medium, and the hyphae or spores are inoculated into the medium for solid culturing under aerobic conditions. The culturing temperature is kept at 0-40° C., preferably 10-35° C. and more preferably 15-30° C. for cell growth and spore formation. The culturing temperature may be changed during the course of culturing, and for example, growth at 25° C. may be followed by culturing at 5° C.

After confirming spore formation, sterilized water is added to the solid cultured hyphae and the mixture is agitated by an ordinary method to obtain a spore suspension. There are no particular restrictions on the additives in the added sterilized water, and instead of purified water there may be used water containing added surfactants, inorganic salts or the like, or prepared saline may be used. The agitating method may involve simple application of external force to the solid culturing vessel, or force may be applied directly to the hyphae with a sterilized brush or the like.

The spore suspension or suspension of spores and hyphae which is obtained in this manner is used as the preservation stock solution. The preservation stock solution may also be diluted with sterilized water or with a solution containing surfactants or inorganic salts for preparation of the final preservation stock solution. Next, a cryoprotectant is added to the preservation stock solution. The cryoprotectant is not particularly restricted so long as it is a commonly used one, and there may be added one or more selected from among agar powder, fetal bovine serum, DMSO, glycerin, inositol, polyvinyl alcohol, skim milk and the like. As a specific example, glycerin may be added to the cryoprotectant to a glycerin concentration of 10% in the preservation solution.

After adding the cryoprotectant, the preservation solution is dispensed into a preservation container. The container is suitably a sterilized plastic tube or the like. As a specific example, the preservation solution is dispensed into a 1.2 mL volume cryogenic vial by a sterile procedure. Next, the preservation solution is stored in an ultra low temperature freezer. The temperature inside the ultra low temperature freezer is controlled to a range of between −100° C. and −20° C., preferably between −90° C. and −30° C. and more preferably between −85° C. and −50° C.

The cells stored in the ultra low temperature freezer in this manner can be stably preserved for long periods.

When the preserved cells are to be used for culturing, the preservation solution is first thawed. The thawing should be carried out as rapidly as possible, preferably within 30 minutes at a temperature of no higher than 40° C., more preferably within 30 minutes at a temperature of no higher than 30° C. and even more preferably within 10 minutes at a temperature of no higher than 30° C.

The preservation solution thawed in this manner is transferred to liquid medium for culturing. The carbon source used may be a common one such as glucose, fructose, xylose, saccharose, maltose, soluble starch, molasses, glycerol, mannitol or saccharified starch, although there is no limitation to these.

As nitrogen sources there may be used natural nitrogen sources such as peptone, yeast extract, malt extract, meat extract, casamino acid, corn steep liquor, soybean protein, defatted soybean and cotton seed meal, as well as organic nitrogen sources including urea or inorganic nitrogen sources such as sodium nitrate, ammonium nitrate and ammonium sulfate, among which there may be particularly mentioned nitrogen sources obtained from soybean, and specifically soybean, defatted soybean, soybean flakes, edible soybean protein, okara, soy milk, soy flour and the like. Especially preferred for use is heat denatured defatted soybean, and more preferably one or more different types of defatted soybean heat treated at about 70-90° C. and depleted of the ethanol-soluble components, optionally in combination with any of the nitrogen sources mentioned above.

If necessary, trace nutrients including phosphate ion, potassium ion, sodium ion, magnesium ion or calcium ion, metal ions such as iron, copper, zinc, manganese, nickel or cobalt, or vitamins may also be added. Such medium components are not particularly restricted so long as they are in concentrations which do no interfere with growth of the microorganism. For practical applications, the carbon source is generally added at a total concentration of 0.1-40 wt % and preferably 1-25 wt % and the nitrogen source at a total concentration of 2-15 wt % and preferably 2-10 wt %, and especially an initial carbon source addition of 1-5 wt % and an initial nitrogen source addition of 3-8 wt %, with further feeding of the carbon and nitrogen sources (more preferably the carbon source alone) during culturing.

The yield of the PUFA-containing fat or oil can be increased by using an unsaturated fatty acid precursor, for example, a hydrocarbon such as hexadecane or octadecane; a fatty acid such as oleic acid or linoleic acid or a salt thereof, a fatty acid ester such as an ethyl ester, glycerin fatty acid ester or sorbitan fatty acid ester, or a fat or oil such as olive oil, soybean oil, rapeseed oil, cottonseed oil or coconut oil, either alone or in combinations. Addition of the substrate may be at 0.001-10% and preferably 0.05-10% with respect to the medium. Such substrates may also be used as the sole carbon source for culturing.

The culturing temperature for the microorganism which produces the PUFA-containing fat or oil will differ depending on the microorganism used, and may be 5-40° C. and preferably 20-30° C., or cells grown by culturing at 20-30° C. may be subsequently cultured at 5-20° C. to produce PUFA-containing fats and oils. Such temperature control can also increase the proportion of PUFAs of the constituent fatty acids in the PUFA-containing fats and oils. Seed culturing may be carried out by jar fermenter culturing, shake culturing or stationary liquid culturing, and jar fermenter culturing is carried out for the main culturing. The medium pH at the start of the main culturing (upon transfer of the seed culture) is adjusted to 5-7, and preferably 5.5-6.5. The culturing period for each stage of seed culturing will normally be 1-10 days, preferably 1-5 days and more preferably 1-3 days. The culturing period for the main culturing will normally be 2-30 days, preferably 5-20 days and more preferably 5-15 days.

Microorganisms belonging to the genus *Mortierella* subgenus *Mortierella* are known to produce compounds comprising arachidonic acid as the main constituent fatty acid (fats and oils (arachidonic acid-containing triglycerides) and/or arachidonic acid-containing phospholipids), but through mutagenesis of the aforementioned strain, the present inventors have succeeded in obtaining a microorganism capable of producing fats and oils comprising dihomo-γ-linolenic acid as the main constituent fatty acid (Japanese Unexamined Patent Publication HEI No. 5-91887), and microorganisms capable of producing fats and oils comprising ω9 polyunsaturated fatty acids as the main constituent fatty acids (Japanese Unexamined Patent Publication HEI No. 5-91888).

In addition, we have obtained microorganisms having resistance to high-concentration carbon sources (Japanese Unexamined Patent Publication HEI No. 5-9188, Japanese Unexamined Patent Publication HEI No. 10-57085, Japanese Unexamined Patent Publication HEI No. 5-91886), which are fungi belonging to the genus *Mortierella* subgenus *Mortierella* and capable of producing PUFA-containing fats and oils and/or PUFA-containing phospholipids by culturing using preserved strains which have been stored by the culturing method, and specifically the novel preserved cell preparation method and storage method, according to the invention. However, the present invention is not limited to fungi belonging to the genus *Mortierella* subgenus *Mortierella*, and the culturing method of the invention may be applied to microorganisms capable of producing compounds comprising polyunsaturated fatty acids as constituent fatty acids (fats and oils (triglycerides) and/or phospholipids), to obtain the intended microbial biomass, crude oils and/or crude phospholipids, and refined fats and oils and/or refined phospholipids obtained by refining of the crude oils and/or crude phospholipids.

The method for obtaining the crude oil and/or crude phospholipid from microorganisms having the fat or oil accumulated in the cells may involve treating the fully cultured solution directly or after sterilization, concentration and acidification, and then recovering the cultured cells by ordinary solid/liquid separation means such as natural precipitation, centrifugal separation and/or filtration. The solid/liquid separation can be aided by addition of an aggregating agent or filtering aid. Examples of aggregating agents include aluminum chloride, calcium chloride, algin and chitosan. Diatomaceous earth may be mentioned as a filtering aid. The cultured cells are preferably rinsed, ruptured and dried. The drying may be carried out by freeze drying, blow drying, fluidized bed drying or the like.

The means for recovering the crude oil and/or crude phospholipids from the dried cells may be an organic solvent extraction method or a pressing method, but extraction with an organic solvent under a nitrogen stream is preferred. As organic solvents there may be used ethanol, hexane, methanol, chloroform, dichloromethane, petroleum ether, acetone and the like, or there may be employed alternating extraction with methanol and petroleum ether, or a single-layer solvent system of chloroform-methanol-water. However, the extraction method used to obtain the crude oil and/or crude phospholipid is not limited to the method described above and may instead be any method which accomplishes efficient extraction of cellular fats and oils (triglycerides) and/or phospholipids. For example, extraction with a supercritical $CO_2$ flow may be employed as an effective means.

By reduced pressure removal of the organic solvent or the supercritical flow components from the extract obtained by extraction using the organic solvent or supercritical flow, it is possible to obtain the target crude oils and/or crude phospholipids. In this case as well, the crude oils and/or crude phospholipids may be extracted by the same method as from dried cells, but the extraction efficiency may be greater by using a water-compatible solvent such as methanol, ethanol or acetone, or a water-compatible mixture comprising any of these with water and/or another solvent.

The microbial biomass containing polyunsaturated fatty acids as constituent fatty acids obtained according to the invention, or the crude oils and/or crude phospholipids, may be used directly by incorporation into animal feeds. For applications to foods, however, a common fat/oil refining process is preferably used. The fat/oil refining process used may be an ordinary process such as degumming, deoxidation, deodorization, decolorizing, column treatment, molecular distillation, wintering or the like.

An unlimited number of uses exist for the microbial biomass, crude oils, refined fats and oils (triglycerides), crude phospholipids and refined phospholipids of the invention: for example, they may be used as starting materials and additives for foods, beverages, cosmetics and pharmaceuticals. The purposes of use and amounts of use are also completely unrestricted.

As examples of food compositions there may be mentioned ordinary foods, as well as functional foods, nutritional supplements, premature infant modified milk, mature infant modified milk, nursing infant modified milk, infant foods, maternal foods or geriatric foods. As examples of fat/oil-containing foods there may be mentioned natural fat/oil-containing foods such as meat, fish and nuts, foods to which fats/oils are added during preparation, such as soups, foods employing fats/oils as heating media, such as donuts, fat and oil foods such as butter, processed foods to which fats/oils are added during processing, such as cookies, or foods which are sprayed or coated with fats/oils upon finishing, such as hard biscuits. Such compositions may also be added to agricultural foods, fermented foods, livestock feeds, marine foods and beverages which contain no fats or oils. They may also be in the form of functional foods or pharmaceuticals, and for example, in processed forms such as enteral nutrients, powders, granules, lozenges, oral solutions, suspensions, emulsions, syrups and the like.

EXAMPLES

The present invention will now be explained in greater detail by the following examples, with the understanding that the invention is not limited thereto.

Example 1

Method for Cryopreservation of Spore Suspension

*Mortierella alpina* 1S-4 was used as an arachidonic acid-producing strain. Stationary culturing was carried out for 7 days at 25° C. at a slant in Czapek agar medium (adjusted to pH 6.0 and sterilized) provided in a test tube, and after confirming hyphal growth, the test tube was stored in a refrigerator (4° C.) for 10 days.

Sterilized water was added to the test tube and the mixture was well agitated to prepare a spore suspension. The spore suspension was appropriately diluted and coated onto a potato dextrose agar medium plate, and a colony counting method was used to count the spores in the spore suspension, giving a result of 1×10$^6$ spores/mL. Next, the spore suspension was diluted 100-fold with sterilized water. The diluted spore suspension, glycerin and water were mixed in the following proportion: diluted spore suspension:glycerin:water=1:1:8 (by volume) (the water and glycerin were premixed and sterilized). A 1 mL portion of the mixture was placed in a 1.2 mL volume sterilized cryogenic vial and cryopreserved in an ultra low temperature freezer at −80° C.

For use of the *M. alpina* in liquid culture, the cryopreserved strain was rapidly thawed in a 25° C. incubator and transferred to the liquid culture.

Comparative Example 1

Method for Preparation of Spore Suspension

*Mortierella alpina* 1S-4 was used as an arachidonic acid-producing strain. Stationary culturing was carried out for 7 days at 25° C. at a slant in Czapek agar medium (adjusted to pH 6.0 and sterilized) provided in a test tube, and after confirming hyphal growth, the test tube was stored in a refrigerator.

For use of the *M. alpina* 1S-4 in liquid culture, sterilized water was added to the test tube and the mixture was agitated well to prepare a spore suspension. The spore suspension was transferred to liquid medium.

Example 2

Culturing Experiment, Difference in Reproducibility by Preservation Method

Culturing was carried out from a seed strain prepared by the method of Example 1 and Comparative Example 1 using *M. alpina* 1S-4.

After transferring 0.1 vol % of the preserved seed strain to medium at pH 6.3 containing 1.0% yeast extract and 2.0% glucose, seed culturing was initiated under conditions of 100 rpm reciprocal shaking, 28° C. temperature, and culturing was continued for 3 days.

Next, 25 L of medium at pH 6.3 containing 5.0% defatted soybean powder, 0.3% $KH_2PO_4$, 0.1% $Na_2SO_4$, 0.05% $CaCl_2 \cdot 2H_2O$, 0.05% $MgCl_2 \cdot 6H_2O$, 1.8% glucose and 0.1% soybean oil was prepared in a 50 L volume jar fermenter, and then 100 mL of the seed culture solution was transferred and culturing was initiated under conditions of 92 rpm agitation, 26° C. temperature, 200 kPa internal pressure and 12.5 L/min airflow. During the culturing, glucose was added at the concentration shown in Table 1, and culturing was continued for 10 days.

TABLE 1

Time and concentration of glucose feeding (concentration with respect to culture solution)

| Feeding time | Feeding concentration |
| --- | --- |
| 1st day | 4.5% |
| 2nd day | 4.5% |
| 3rd day | 4% |
| 4th day | 3% |
| 5th day | 3% |
| 6th day | 1% |

Culturing was carried out several times by the same method, at different days after initiating seed strain preservation. The yields of arachidonic acid obtained on the 10th day of culturing for each culture are shown in Table 2.

In the case of the seed strain prepared and preserved by the method of Example 1, the arachidonic acid yield reproducibility was satisfactory for each culture. However, poor reproducibility for each culture resulted when using the seed strain prepared and preserved by the method of Comparative Example 1.

TABLE 2

Results

| | Seed strain preparation method | |
| --- | --- | --- |
| | Spore suspension cryopreservation (Method of Example 1) | Preparation of spore suspension by slant (Method of Comp. Example 1) |
| | Seed strain preservation method | |
| | Cryopreservation of spore suspension | Refrigeration of Czapek agar medium slant solid-cultured hyphae |
| Days of preservation | 1 day | 1 day |
| Arachidonic acid yield | 13.9 g/L | 13.8 g/L |
| Days of preservation | 30 days | 30 days |
| Arachidonic acid yield | 13.0 g/L | 13.5 g/L |
| Days of preservation | 30 days | 30 days |
| Arachidonic acid yield | 14.2 g/L | 10.5 g/L |
| Days of preservation | 60 days | 60 days |
| Arachidonic acid yield | 12.9 g/L | 14.2 g/L |
| Days of preservation | 60 days | 60 days |
| Arachidonic acid yield | 13.6 g/L | 10.5 g/L |
| Days of preservation | 90 days | 90 days |
| Arachidonic acid yield | 13.5 g/L | 13.5 g/L |
| Days of preservation | 90 days | 90 days |
| Arachidonic acid yield | 14.1 g/L | 10.1 g/L |

Example 3

Culturing Experiment, Change in Productivity with Prolonged Preservation

Culturing was carried out from a seed strain prepared by the method of Example 1 and Comparative Example 1 using *M. alpina* 1S-4.

After transferring 0.1 vol % of the preserved seed strain to medium at pH 6.3 containing 1.0% yeast extract and 2.0% glucose, seed culturing was initiated under conditions of 100 rpm reciprocal shaking, 28° C. temperature, and culturing was continued for 3 days.

Next, 25 L of medium at pH 6.3 containing 1.0% yeast extract, 1.8% glucose and 0.1% soybean oil was prepared in a 50 L volume jar fermenter, and then 100 mL of the seed culture solution was transferred and culturing was initiated under conditions of 200 rpm agitation, 28° C. temperature, 150 kPa internal pressure and 25 L/min airflow. During the culturing, glucose was added at the concentration shown in Table 3, and culturing was continued for 7 days.

TABLE 3

Time and concentration of glucose feeding (concentration with respect to culture solution)

| Feeding time | Feeding concentration |
| --- | --- |
| 1st day | 1.5% |
| 2nd day | 1.5% |

TABLE 3-continued

Time and concentration of glucose feeding (concentration with respect to culture solution)

| Feeding time | Feeding concentration |
|---|---|
| 3rd day | 1% |
| 4th day | 1% |

Culturing was carried out several times by the same method, at different days after initiating seed strain preservation. The yields of arachidonic acid obtained on the 7th day of culturing for each culture are shown in Table 4.

In the case of the seed strain prepared and preserved by the method of Example 1, the arachidonic acid productivity was satisfactorily reproduced even with prolonged preservation. In the case of the seed strain prepared and preserved by the method of Comparative Example 1, however, the arachidonic acid productivity tended to fall during prolonged preservation.

TABLE 4

| Results | | |
|---|---|---|
| | Seed strain preparation method | |
| | Spore suspension cryopreservation (Method of Example 1) | Preparation of spore suspension by slant (Method of Comp. Example 1) |
| | Seed strain preservation method | |
| | Cryopreservation of spore suspension | Refrigeration of Czapek agar medium slant solid-cultured hyphae |
| Days of preservation | 1 day | 1 day |
| Arachidonic acid yield | 3.7 g/L | 3.6 g/L |
| Days of preservation | 4 years | 4 years |
| Arachidonic acid yield | 4.0 g/L | 2.5 g/L |
| Days of preservation | 8 years | 8 years |
| Arachidonic acid yield | 3.9 g/L | 2.2 g/L |

Example 4

Effect of Spore-Forming Medium pH

*M. alpina* 1S-4 was used as an arachidonic acid-producing strain. Two different Czapek agar media with different pH, having the compositions shown in Table 5, were prepared in test tubes. The pH of the Czapek medium without pH adjustment was measured to be 8.5.

TABLE 5

| | pH adjusted (6.0) | No pH adjustment (*2) |
|---|---|---|
| Sodium nitrate (NaNO₃) | 2 g/L | 2 g/L |
| Dipotassium hydrogen phosphate (K₂HPO₄) | 1 g/L | 1 g/L |
| Magnesium sulfate heptahydrate (MgSO₄·7H₂O) | 0.5 g/L | 0.5 g/L |
| Potassium chloride (KCl) | 0.5 g/L | 0.5 g/L |
| Iron (II) sulfate heptahydrate (FeSO₄·7H₂O) | 0.01 g/L | 0.01 g/L |
| Saccharose | 30 g/L | 30 g/L |
| Agar powder | 13 g/L | 13 g/L |
| HCl solution | Added (*1) | Not added |

(*1) Added for pH adjustment to 6.0
(*2) Measured pH: 8.5.

One loop each of the hyphae was transferred to two agar media of different pH and stationary culturing was carried out at 25° C. for 7 days, and after confirming hyphal growth, the test tubes were stored in a refrigerator (4° C.) for 10 days.

Sterilized water was added to each of the test tubes and the mixture was well agitated to prepare a spore suspension. The spore suspension was appropriately diluted and coated onto a potato dextrose agar medium plate, and a colony counting method was used to count the spores in the spore suspension, giving a result of $1 \times 10^6$ spores/mL obtained in the agar medium at pH 6.0, and $5 \times 10^4$ spores/mL obtained in the medium without pH adjustment (measured pH: 8.5).

Spore suspensions prepared by both of these methods were used for culturing by the method of Example 3, and the arachidonic acid yields were compared. As a result, an arachidonic acid yield of 3.5 g/L was obtained from the spore suspension produced in the medium adjusted to pH 6.0, and an arachidonic acid yield of 2.9 g/L was obtained from the medium without pH adjustment (measured pH: 8.5).

Example 5

Cryopreservation System

Example 1 was repeated but with the preserved spore suspension prepared in a 1.2 mL volume cryogenic vial stored in a −20° C. freezer for condition (5-1), in a −80° C. ultra low temperature freezer for condition (5-2) and in liquid nitrogen (approximately −196° C.) for condition (5-3). After 30 days of storage under these three conditions, culturing was carried out in the same manner as Example 2. As a result, both the spore survival rate and arachidonic acid productivity were superior under the condition of storage in a −80° C. ultra low temperature freezer.

TABLE 6

| | Condition | | |
|---|---|---|---|
| | 5-1 −20° C. storage | 5-2 −80° C. storage | 5-3 Liquid nitrogen storage |
| Number of spores after thawing | $2 \times 10^2$ spores/mL | $9 \times 10^3$ spores/mL | $1 \times 10^2$ spores/mL |
| Arachidonic acid yield | 9.1 g/L | 13.0 g/L | 8.7 g/L |

Example 6

Corroboration of Culturing Reproducibility of Frozen Strain by Large Tank Culturing Culturing was carried out from a seed strain prepared by the method of Example 1 using *M. alpina* 1S-4.

After transferring 0.1 vol % of the preserved strain to medium at pH 6.3 containing 1.0% yeast extract and 2.0% glucose, seed culturing was initiated under conditions of 100 rpm reciprocal shaking, 28° C. temperature (1st stage), and culturing was continued for 3 days.

Next, 30 L of medium at pH 6.3 containing 1% yeast extract, 2% glucose and 0.1% soybean oil was prepared in a 50 L volume jar fermenter, and then the seed culture (1st stage) solution was transferred and seed culturing (2nd stage) was initiated under conditions of 200 rpm agitation, 28° C. temperature, 150 kPa internal pressure and 12.5 L/min airflow, for 2 days of culturing.

Next, 4500 L of medium (Medium A: 336 kg soybean powder, 16.8 kg $KH_2PO_4$, 2.8 kg $MgCl_2.6H_2O$, 2.8 kg $CaCl_2.2H_2O$, 5.6 kg soybean oil) was adjusted to a pH of 4.5 and sterilized under conditions of 121° C., 20 minutes. As a separate medium there was prepared Medium C by sterilizing 1000 L of medium (Medium B: 112 kg hydrous glucose) at 140° C. for 40 seconds and adding it to the previous Medium A. After adjusting Medium C to pH 6.3, a 28 L volume of the seed culture (2nd stage) was transferred, for a combined total of 5600 L of initial culture solution (10 kL volume culturing tank).

For transfer of the seed culture solution (2nd stage) to the main culturing medium, vapor was passed through the tube connecting the seed culturing tank and the main culturing tank for sterilization (≥30 min at 121-126° C.), and then sterile air was introduced through the tube for cooling to a tube surface temperature of below 60° C. After cooling, the seed culture (2nd stage) was allowed passage and transported in a prescribed volume to the main culturing tank. When transfer of the seed culture to the main culturing medium was completed, culturing was initiated at a temperature of 26° C., an airflow quantity of 49 $Nm^3$/hr and an internal pressure of 200 kPa. The medium was fed during the culturing according to the schedule shown in the following table, for 306 hours of main culturing. When the culturing was complete, the culture volume was 7750 L as a result of the increase by medium feeding and loss by evaporation. The arachidonic acid yield per culture upon completion of culturing was 18.2 g/L.

| Main culturing time | Feeding medium |
| --- | --- |
| After 19 hrs | 280 kg hydrous glucose/460 L |
| After 43 hrs | 280 kg hydrous glucose/450 L |
| After 67 hrs | 252 kg hydrous glucose/390 L |
| After 91 hrs | 252 kg hydrous glucose/410 L |
| After 120 hrs | 224 kg hydrous glucose/370 L |
| After 140 hrs | 168 kg hydrous glucose/280 L |
| After 163 hrs | 168 kg hydrous glucose/270 L |

After completion of culturing, sterilization was carried out under conditions of 120° C., 20 minutes, and then the wet cell mass was recovered with a continuous dehydrator and dried to a moisture content of 1 wt % with an oscillating fluidized bed drier, and the dried cells were transported to a packing location using an air conveyor. The obtained dry cell mass was packed into an approximately 1 $m^3$ volume aluminum pouch container bag together with nitrogen gas, and the mouth of the bag was heat sealed prior to storage in a cold storage room at below 10° C.

After removal from the container bag, the dry cell mass was subjected to hexane extraction and the hexane solution was filtered to remove the solid portion, after which it was heated under reduced pressure to remove the hexane and obtain a crude oil comprising arachidonic acid as a constituent fatty acid.

The same culturing was repeated three times. The results for the arachidonic yields upon completion of culturing are summarized in Table 7. The reproducibility of the preserved strain was satisfactory, thus confirming that more stable arachidonic acid productivity had been achieved.

TABLE 7

Summary of arachidonic acid yields upon completion of culturing

| Culturing | |
| --- | --- |
| 1 | 18.2 g/L |
| 2 (1 year later) | 17.8 g/L |
| 3 (5 years later) | 17.9 g/L |

Example 7

Corroboration of Culturing Reproducibility of Frozen Dihomo-γ-Linolenic Acid-Producing Strain

*Mortierella alpina* SAM1860 was used as a dihomo-γ-linolenic acid-producing strain. Stationary culturing was carried out for 12 days at 25° C. at a slant in Czapek agar medium (adjusted to pH 6.0 and sterilized) provided in a test tube, and after confirming hyphal growth, the test tube was stored in a refrigerator (4° C.) for 20.days.

Sterilized water was added to the test tube and the mixture was well agitated to prepare a spore suspension. The spore suspension was appropriately diluted and coated onto a potato dextrose agar medium plate, and a colony counting method was used to count the spores in the spore suspension, giving a result of $5 \times 10^6$ spores/mL.

Next, the spore suspension was diluted 100-fold with sterilized water. The diluted spore suspension, glycerin and sterilized water were mixed in the following proportion: diluted spore suspension:glycerin:sterilized water=1:1:8 (by volume). A 1 mL portion of the mixture was placed in a 1.2 mL volume sterilized cryogenic vial and cryopreserved for one month in an ultra low temperature freezer at −80° C.

As a comparative example, a spore suspension prepared by the same method was stored for one month in a refrigerator (5° C.).

The two preserved strains stored for one month were used for culturing by the same method as in Example 3. As a result, the DGLA yields were as shown in Table 8, indicating the effectiveness of the cryopreservation method.

TABLE 8

| | Results | |
| --- | --- | --- |
| Seed strain preparation method | Cryopreservation of spore suspension | Refrigeration of spore suspension |
| DGLA yield | 3.1 g/L | 2.7 g/L |

Example 8

Corroboration of Culturing Reproducibility of Other Frozen Arachidonic Acid-Product Strains

*Mortierella elongata* IFO8570 and *Mortierella alpina* CBS754.68 were used as arachidonic acid-producing strains.

Stationary culturing was carried out for 10 days at 25° C. at a slant in Czapek agar medium (adjusted to pH 6.0 and sterilized) provided in a test tube, and after confirming hyphal growth, the test tube was stored in a refrigerator (4° C.) for 20 days.

Sterilized water was added to the test tube and the mixture was well agitated to prepare a spore suspension. The spore suspension was diluted 10-fold with sterilized water. The diluted spore suspension, glycerin and sterilized water were mixed in the following proportion: diluted spore suspension: glycerin:sterilized water=1:1.5:7.5 (by volume). A 1 mL portion of the mixture was placed in a 1.2 mL volume sterilized cryogenic vial and cryopreserved for one month in an ultra low temperature freezer at −80° C.

As a comparative example, a spore suspension prepared by the same method was stored for one month in a refrigerator (5° C.).

Each of the four preserved strains stored for one month (two different strains×two different preservation methods) was transferred to a medium at pH 6.3 containing 1% yeast extract and 2% glucose, and used for 3 days of seed culturing under conditions of 100 rpm reciprocal shaking, 28° C. temperature.

Next, 25 L of medium (500 g glucose, 775 g defatted soybean powder, 50 g $KH_2PO_4$, 7.5 g/L $MgCl_2 \cdot 6H_2O$, 7.5 g/L $CaCl_2 \cdot 2H_2O$, 25 g soybean oil, pH 6.0) was prepared in a 50 L volume jar fermenter, and then the seed culture solution was transferred and main culturing was initiated under conditions of 200 rpm agitation, 28° C. temperature and 150 kPa internal pressure. The culturing was continued for 186 hours, while adding a 50% glucose solution approximately every 24 hours for a glucose concentration of about 1.2%. As a result, the arachidonic acid yields shown in Table 9 were obtained, indicating the effectiveness of the cryopreservation method.

TABLE 9

| Seed strain preparation method Arachidonic acid yield | Cryopreservation of spore suspension | Refrigeration of spore suspension |
|---|---|---|
| M. elongata IFO8570 | 3.4 g/L | 2.0 g/L |
| M. alpina CBS754.68 | 7.2 g/L | 5.1 g/L |

Example 9

Comparison of L-Drying Method and Cryopreservation Method for 9-Year Stored Samples A spore suspension was prepared, and dry spore ampules were created and preserved by the conventionally known L-drying method ("Maintaining cultures for Biotechnology and Industry (1996)", edited by J. C. Hunter-Cevera & A. Belt, Academic Press, p. 115). After creation and storage for 9 years, the six L-dried ampules were opened and their contents restored and coated onto agar medium, and the number of surviving spores were counted. Likewise, the six 1.2 mL volume cryogenic vials prepared by the method of Example 1 (and cryopreserved for 9 years) were opened, and the number of surviving spores was counted.

The results shown in the table below confirmed that the preservation method according to Example 1 resulted in a notably superior survival rate compared to the L-drying method of the prior art. It was concluded that the method of the invention is a highly effective method for prolonged preservation of microbial strains.)

TABLE 10

| Condition | L-drying method | Cryopreservation |
|---|---|---|
| Number of surviving ampules | 3 ampules survived 3 ampules died | All 6 tubes survived |
| Number of surviving spores | 2 in surviving ampules 0 in dead ampules | 200 in tube |

The invention claimed is:

1. A method for preservation of a spore-forming microorganism capable of microbial production of a polyunsaturated fatty acid or a compound comprising a polyunsaturated fatty acid as a constituent fatty acid, wherein the spore-forming microorganism is *Mortierella alpina*, which method comprises:
   (a) culturing the microorganism in a spore-forming medium at pH 4-7 containing a nutrient source comprising an inorganic salt and a saccharide, wherein the microorganism forms spores;
   (b) suspending the spores obtained in (a) in sterilized water, or sterilized water containing a surfactant and/or an inorganic salt to prepare a spore suspension, and adding a cryoprotectant at 5-15% to prepare a cryopreserving spore suspension; and
   (c) preserving the cryopreserving spore suspension obtained in (b) at between −100° C. and −20° C.

2. A method according to claim 1, wherein said inorganic salt is at least one type of inorganic salt selected from the group consisting of sodium nitrate, dipotassium hydrogen phosphate, magnesium sulfate, potassium chloride and iron (II) sulfate.

3. A method according to claim 1, characterized in that said spore-forming medium is Czapek agar medium or Czapek-Dox agar medium adjusted to a pH of 4-7 with hydrochloric acid and/or sulfuric acid.

4. A method according to claim 1, characterized in that said cryoprotectant is glycerin.

5. A method for preservation of a microorganism according to claim 1, wherein the microorganism is capable of producing a triglyceride comprising a polyunsaturated fatty acid as a constituent fatty acid or a phospholipid comprising a polyunsaturated fatty acid as a constituent fatty acid.

6. A method for preservation of a microorganism according to claim 1, wherein the microorganism is capable of producing an ω6 unsaturated fatty acid, ω3 polyunsaturated fatty acid, ω9 polyunsaturated fatty acid, or a combination thereof, or a compound comprising an ω6 unsaturated fatty acid, ω3 polyunsaturated fatty acid, ω9 polyunsaturated fatty acid, or a combination thereof.

7. A method for preservation of a microorganism according to claim 6, wherein the ω6 unsaturated fatty acid is 9,12-octadecadienoic acid (linoleic acid) 18:2ω6, 6,9,12-octadecatrienoic acid (γ-linolenic acid) 18:3ω6, 8,11,14-eicosatrienoic acid (dihomo-γ-linolenic acid) 20:3ω6, 5,8,11,14-eicosatetraenoic acid (arachidonic acid) 20:4ω6, 7,10,13,16-docosatetraenoic acid 22:4ω6 or 4,7,10,13,16-docosapentaenoic acid 22:5ω6.

8. A method for preservation of a microorganism according to claim 6, wherein the ω3 unsaturated fatty acid is 9,12,15-octadecatrienoic acid α-linolenic acid) 18:3ω3, 6,9,12,15-octadecatetraenoic acid (stearidonic acid) 18:4ω3, 11,14,17-eicosatrienoic acid (dihomo-α-linolenic acid) 20:3ω3, 8,11,14,17-eicosatetraenoic acid 20:4ω3, 5,8,11,14,17-eicosapentaenoic acid 20:5ω3, 7,10,13,16,19-docosapentaenoic acid 22:5ω3 or 4,7,10,13,16,19-docosahexaenoic acid 22:6ω3.

9. A method for preservation of a microorganism according to claim 6, wherein the ω9 unsaturated fatty acid is 6,9-octadecadienoic acid 18:2ω9, 8,11-eicosadienoic acid 20:2ω9 or 5,8,11-eicosatrienoic acid (Mead acid) 20:3ω9.

* * * * *